United States Patent [19]
Pause

[11] Patent Number: 5,907,091
[45] Date of Patent: May 25, 1999

[54] PROCEDURE AND DEVICE FOR THE MEASUREMENT OF WATER VAPOR TRANSFER THROUGH TEXTILES AND OTHER PLATE-LIKE MATERIALS

[76] Inventor: Barbara Hildegard Pause, 8076 Dry Creek Cir., Longmont, Colo. 80503

[21] Appl. No.: 08/954,017

[22] Filed: Oct. 20, 1997

[30] Foreign Application Priority Data

Oct. 26, 1996 [DE] Germany .......................... 196 44 575

[51] Int. Cl.$^6$ .......................... G01N 13/04; G01N 15/08; C12M 1/12; G01M 3/16
[52] U.S. Cl. .................................. 73/38; 73/29.01; 73/40
[58] Field of Search ............................. 73/38, 40, 29.01, 73/73

[56] References Cited

U.S. PATENT DOCUMENTS

| | | | |
|---|---|---|---|
| 3,498,110 | 3/1970 | Brun | 73/38 |
| 3,604,246 | 9/1971 | Toren | 73/38 |
| 4,194,041 | 3/1980 | Gore et al. | 428/315 |
| 5,048,336 | 9/1991 | Sugihara et al. | 73/336.5 |
| 5,390,539 | 2/1995 | Mayer | 73/38 |
| 5,483,078 | 1/1996 | Hermann et al. | 250/559.32 |
| 5,535,615 | 7/1996 | Kent et al. | 73/38 |
| 5,590,790 | 1/1997 | Saunders | 209/534 |
| 5,591,636 | 1/1997 | Grass | 435/287.1 |
| 5,659,130 | 8/1997 | Chung et al. | 73/64.47 |

Primary Examiner—Hezron Williams
Assistant Examiner—J. David Wiggns

[57] ABSTRACT

The invention provides a method for measurement of characteristics related to water vapor transfer through plate-like material samples, in particular textile materials, and a measuring unit device with a water container, a water container atmosphere or headspace, air chamber, and measuring chamber, where the water container headspace and air chamber are separated by such plate-like material sample for carrying out such measurements under stationary air flow conditions according to detecting an absolute humidity increase of 1% in an air chamber atmosphere, and where determinations of water vapor transmission rate, water vapor resistance, water vapor permeability and water vapor pressure differential across the plate-like material sample are obtained via use of appropriate sensors installed within the housing of such testing device, including air temperature and humidity sensors, water temperature sensor, and an evaporative heat flux thermal sensor.

16 Claims, 1 Drawing Sheet

PROCEDURE AND DEVICE FOR THE MEASUREMENT OF WATER VAPOR TRANSFER THROUGH TEXTILES AND OTHER PLATE-LIKE MATERIALS

BACKGROUND OF THE INVENTION

Water vapor permeability and water vapor resistance are important elements in the evaluation of the thermophysical wearing comfort of a garment. Knowing the characteristics related to water vapor transfer in a textile or another material is also important for many technical applications.

The measurement of different characteristics related to water vapor transfer are carried out using methods requiring extended measuring intervals. For example, in carrying out the methods of the standard procedures ASTM 96-94 and ISO 11 092, measuring intervals of several hours are necessary. The ASTM 96-94 method is based on a measuring procedure whereby the weight loss of a cup filled with water and covered with the test sample is determined. The weight measurements, repeated at given intervals, and the evaluation of the results, are carried out manually. Thus, the ASTM 96-94 method is considered very labor-intensive. Because of these long measuring times of both methods, routine tests are limited. Furthermore, the tests of the two methods can only be run in a laboratory. Therefore, quality control tests cannot be carried out during production. A critical shortcoming of the standard procedures is also that different measurements are determined under different test conditions so that the results are not comparable.

SUMMARY OF THE INVENTION

The subject of the invention is a procedure and device for the measurement of the water vapor transfer through plate-like samples, in particular textile materials, under various test conditions. The test sample is placed into a measuring chamber atop a container of distilled water. The procedure is based on the measurement of the humidity change in the measuring chamber over time. This humidity change results from the water vapor transfer through the sample due to the difference in water vapor pressure between the sample surfaces. During the measuring procedure, temperature and humidity inside the measuring chamber as well as the water temperature are measured. The evaporative heat flux, the difference in water vapor pressure and the humidity change in a certain period of time are determined from the temperature and humidity measurements. These values are then used to calculate characteristics related to the water vapor transfer such as water vapor transmission rate (WVTR) and water vapor resistance ($R_{et}$).

The measurements can be carried out under variable test conditions. The desired humidity at the beginning of the test is obtained by premoistening or predrying the air in the measuring chamber. For tests requiring temperatures above the ambient temperature, the air in the chamber and the water are preheated by means of a heating system. The measuring procedure is computer-controlled. The process is based on short measuring intervals which makes routine tests especially efficient in terms of both cost and time. The measuring device is portable and easy to handle.

DETAILED DESCRIPTION

Figure 1:
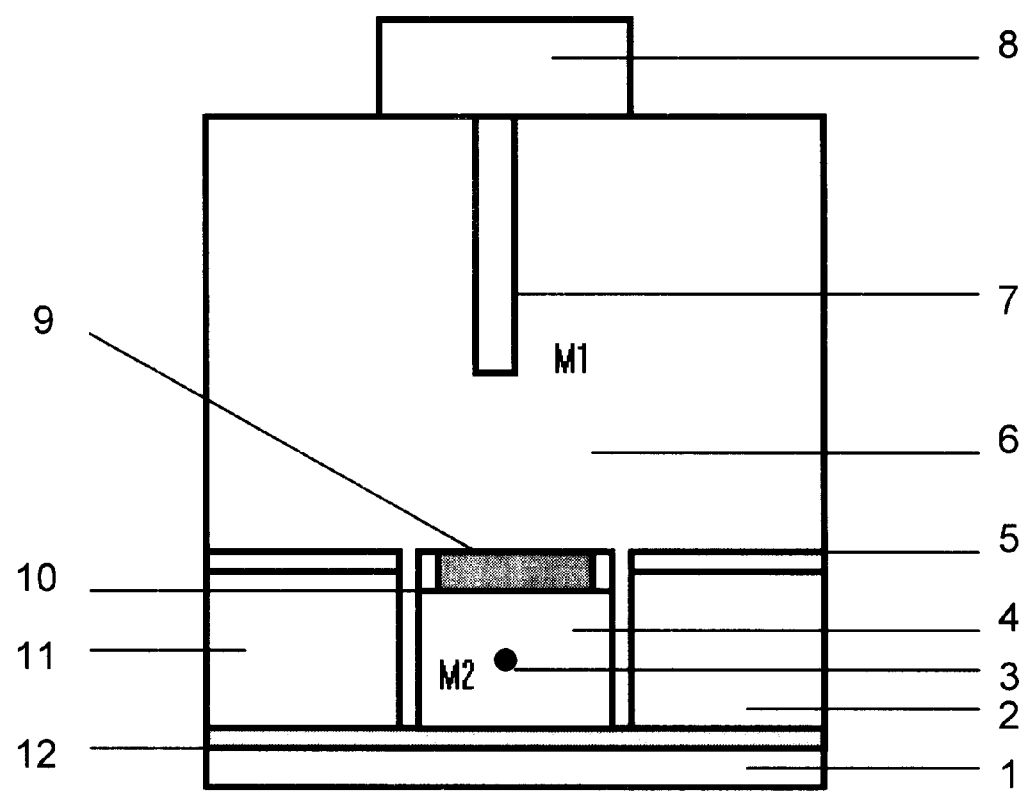
FIG. 1 is a sectional view of the measuring unit.

The subject of the invention is a procedure and device for the determination of characteristics related to water vapor transfer through plate-like samples, in particular textile materials. In this procedure the measuring intervals will be substantially reduced as compared to those necessary with the standard procedures ASTM 96-94 and ISO 11092. Furthermore, by using a highly sensitive measuring technique, accurate and very reproducible results will be obtained. Measurements for samples with various thicknesses can be taken without any loss in accuracy. Compared to other methods, this procedure allows for an substantial reduction in the size of the sample necessary. Because the procedure is controlled by computer the manual aspect of the measurement is substantially reduced.

The purpose of the invention is achieved by the features stated in claims 1 and 9. The Subclaims represent appropriate designs for the measuring procedure and the measuring device. The nature of the invention based on a measuring principle, whereby a humidity change in the chamber air occurs as a result of a water vapor transfer through the sample. This humidity change is measured over time. The characteristics related to water vapor transfer through the sample are calculated from this humidity change within a given time interval, the difference in water vapor pressure between the sample surfaces as well as the evaporative heat flux. During the measuring process, the test sample is placed atop a container of water which is arranged in a measuring chamber possessing a certain volume. At the beginning of the test, the air volume in the measuring chamber possesses a certain humidity. The air temperature in the measuring chamber is equal to the temperature of the water in its container. Because of the differences in water vapor pressure between the container of water and the measuring chamber, i.e. between the two sample surfaces, water vapor transfer through the sample occurs and results in a humidity increase within the measuring chamber. The measurement is taken only until a humidity increase of 1% is obtained, which takes just a few minutes to occur. During the measuring process, not only the humidity increase in the measuring chamber is determined, but the air temperature within the measuring chamber as well as the water temperature are also measured. As a result of the short measuring intervals, the temperatures stay nearly constant during the entire process.

From the temperatures and the chamber humidity at the beginning of the measurement process, the difference in water vapor pressure ($\Delta p$) and the evaporative heat flux ($\phi$) are determined. Furthermore, the absolute humidity gain ($\Delta m_W$) in the air volume within the time interval (t) is calculated using the 'general gas equation'. From these calculated values, the water vapor transmission rate (WVTR) is determined through the formula $$WVTR = \frac{\Delta m_W}{A * t},$$

where A is the sample size. The water vapor resistance ($R_{et}$) is obtained using the formula $$R_{et} = \frac{\Delta t}{WVTR * \varphi}.$$

Finally, the water vapor permeability ($W_D$) of the test samples in reference to the water vapor pressure difference $\Delta p$ is determined using $$W_D = \frac{1}{R_{et} * \varphi}.$$

The determination of the water vapor transfer characteristics is carried out under the desired humidity and temperature conditions, which can be varied. In this way, the measuring results can be compared to those obtained using other testing procedures, provided they have all been carried out under the same testing conditions.

The device according to the invention for the realization of the measuring procedure consists of a measuring unit and a computer system for recording of measuring values and their evaluation. The core of the measuring unit is its measuring chamber (6), at the bottom of which a container (4) filled with distilled water is positioned. The measuring chamber contains a defined air volume. The sample (9), which is fixed onto a sample holder (10) is placed atop the water container in such a way as to completely cover the containers opening. The sample lies on a fine mesh lattice so that a defined amount of water vapor will transfer from the water bath to the sample over a certain period of time. The changing out of a sample is carried out from outside the chamber using a slide-type mechanism. The climatic conditions inside the chamber are not altered during the sample exchange. Until the test procedure is initiated, the sample is separated from the water container and the chamber atmosphere by solid slides to avoid a premature, undesired water vapor transfer through it. As soon as the measurement commences, these slides are removed from the measuring unit by means of the slide mechanism mentioned above.

To establish a desired start humidity inside the chamber prior to measurement initialization, the air in the measuring chamber is premoistened or predryed by means of a moistening/drying system consisting of canisters (2) and (11) containing, respectively, a moistening or drying agent. The appropriate container will be opened when necessary by removing its respective cover plate (5). The desired humidity change is obtained through a humidity compensation process. The measuring chamber as well as the water in the container can be heated by means of a heater (12) located at the bottom (1) of the measuring unit, making possible measurements at temperatures higher than the ambient temperature.

Humidity and temperature in the measuring chamber (6) are determined using a humidity/temperature sensor (7) which possesses a separate amplifier (8) placed atop of the measuring unit. The temperature of the water bath is measured using an additional temperature sensor (3).

The measuring procedure with the proposed device is conducted as follows: First the desired climatic conditions in the measuring chamber are realized by moistening or drying the air within the chamber and, if desired, by preheating the water bath and chamber air. Upon meeting the desired climatic conditions, the canisters of moistening/drying agents are closed and the heater is turned off. At the same time, the measuring program for detection and evaluation of the measuring data and control of the measuring process is downloaded. The sample holder is then removed from the measuring unit and the sample is affixed to it. The sample holder is then slipped back into the measuring unit. After affixing the sample to its holder and manipulating the climatic conditions, the measuring program is initiated. At the same time, the slides are removed are removed from their respective sample surfaces.

The measurement ceases when the humidity inside the measuring chamber increases by 1%. The determination of the characteristics related to water vapor transfer is carried out using specially-designed software. When the measurement is complete, the sample is removed from the measuring unit using the slide-type mechanism.

The invented device requires a minimum of set-up time and is easy to operate. Tests have shown a high rate of reproducibility in the measured results. Another great advantage of this measuring process is the short measuring intervals involved which makes routine tests especially efficient in terms of time and cost. The portable design allows for measurements to be taken from any location, meaning the device can also be implemented during the production process of the material to be tested.

What is claimed:

1. A process for simultaneous determination of two or more characteristics related to water vapor transfer through plate-like samples, in particular textile materials, which requires the steps of:

(a) arranging the test sample atop of a container of water at a certain temperature located at the bottom of a measuring chamber possessing a certain air volume in an air chamber at a certain air temperature and a defined starting humidity;

(b) measuring the humidity change in the measuring chamber over a time interval which occurs when water vapor penetrates the test sample as a result of the difference in water vapor pressure between the water bath and the chamber air;

(c) calculating two or more characteristics related to water vapor transfer using the absolute humidity gain in the air volume within the measuring interval, the difference in water vapor pressure and a thermal measurement of any evaporative heat flux evolved during the water vapor transfer thru such textile test sample.

2. The process according to claim 1 where the characteristics related to water vapor transfer are the water vapor transmission rate, the water vapor resistance and the water vapor permeability.

3. The process according to claim 2 where the water vapor transmission rate is calculated using the absolute humidity gain in the air volume per measuring interval and sample area which is penetrated by the water vapor.

4. The process according to claim 2 where the water vapor resistance is determined using the calculated water vapor transmission rate, the water vapor pressure difference and the evaporative heat flux.

5. The process according to claim 2 where the water vapor permeability is determined using the calculated water vapor resistance and the evaporative heat flux.

6. The process according to claim 1 where the measuring conditions such as starting humidity and air temperature in the measuring chamber as well as the water bath temperature can be varied by moistening or drying the chamber air and by preheating the water bath and the chamber air prior to initiating the measurement process.

7. The process according to claim 1 where a humidity measurement is carried out at point suspended within chamber air of said measuring chamber and the temperature measurements are made at points suspended within chamber air of said measuring chamber and at a location within the water in said container.

8. The process according to claim 1 where the characteristics related to water vapor transfer through the test sample are determined from a very slight variation in humidity within the measuring chamber and under constant air and water temperatures.

9. A measuring unit for measuring characteristics related to water vapor transfer through test samples under stationary air flow conditions, said measuring unit consisting of an open liquid water supply measuring chamber with an overhead air space of chamber air, within which device the following components are situated during an assessment of water vapor permeability properties for said test samples:

a container completely full of water serving also as a water bath, a sample holder for ensuring proper positioning of said test samples, a means for performing a sample exchange between different pairs of said test samples, a temperature measuring sensor for said water bath, air temperature and humidity measuring sensors for said chamber air as well as means used to vary chamber air conditions such as humidity and temperature where said container of water is situated beneath said test samples and is disposed at the bottom of said measuring chamber.

10. The device according to claim 9 in which the sample is affixed to a sample holder in such way as to completely cover the water container and separate the water container and water vapor in a container atmosphere above the level of water in said water container from said measuring chamber.

11. The device according to claim 9 equipped with a slide-type mechanism to carry out the sample exchange, thereby preventing any undesired water vapor transfer prior to measurement initiations.

12. The device according to claim 9 where the sample lies atop a fine mesh lattice during the measurement to maintain a constant water vapor transfer to the sample.

13. The device according to claim 9 where the measuring unit is equipped with a moistening and drying system which is used to obtain a desired starting humidity and to dry the chamber air upon measurement completion and that the moistening and drying system consists of canisters containing chemical solutions immersed therein, and the device includes means to measure, which solutions are covered with plates capable of providing a sealing function, the opening and closing of which is controlled by computer.

14. The device according to claim 9 where the measuring unit is equipped with a heating system for preheating the water bath and chamber air.

15. The device according to claim 9 where the temperature of the water bath is measured with a temperature sensor, and the chamber air temperature and humidity are measured by a second sensor capable of measuring both conditions simultaneously.

16. The device according to claim 9 further having an amplification and a control system as well as a computer for calculating, recording, processing and performing assessment of the measured values including said water temperature, air temperature and humidity conditions, water vapor permeation properties and water vapor transfer characteristics such as water vapor transmission rate and water vapor resistance.

* * * * *